United States Patent [19]
Stokes

[11] 4,271,847
[45] Jun. 9, 1981

[54] TEMPORARY ADJUSTABLE BIPOLAR LEAD

[75] Inventor: Kenneth B. Stokes, Brooklyn Park, Minn.

[73] Assignee: Medtronic, Inc., Minneapolis, Minn.

[21] Appl. No.: 53,001

[22] Filed: Jun. 28, 1979

[51] Int. Cl.³ .............................................. A61N 1/04
[52] U.S. Cl. ................................. 128/786; 128/419 P
[58] Field of Search ................... 128/419 P, 784, 785, 128/786

[56] References Cited

U.S. PATENT DOCUMENTS

| 452,220 | 5/1891 | Gunning | 128/786 |
| 3,485,247 | 12/1969 | Ackerman | 128/786 |
| 3,865,118 | 2/1975 | Bures | 128/786 |

FOREIGN PATENT DOCUMENTS 2605590  8/1977  Fed. Rep. of Germany ....... 128/419 P

*Primary Examiner*—William E. Kamm
*Attorney, Agent, or Firm*—John L. Rooney; Lew Schwartz; Joseph F. Breimayer

[57] ABSTRACT

Temporary adjustable bipolar lead including an inner lead and an outer coaxial lead. A self-sealing lead introducer head at a junction of the inner lead and outer lead provides for takeoff of the end of the outer coaxial lead. The inner lead is in slidable engagement with the outer lead through a hole in a diaphragm of the lead introducer head.

3 Claims, 2 Drawing Figures

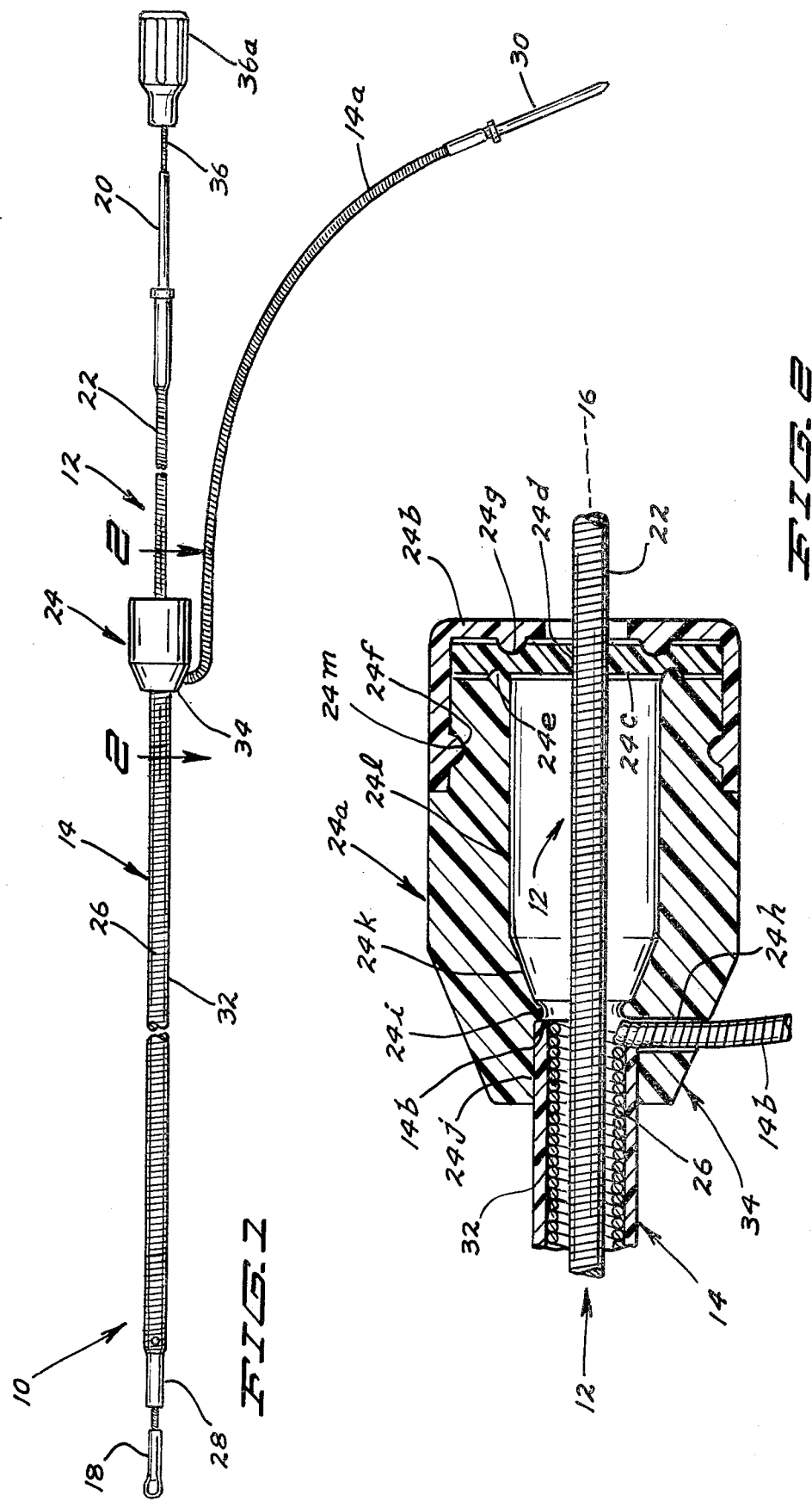

TEMPORARY ADJUSTABLE BIPOLAR LEAD

CROSS-REFERENCES TO CO-PENDING APPLICATIONS

None.

BACKGROUND OF THE INVENTION

1. Field of the Invention

The present invention relates generally to a surgical electrical applicator, and more importantly, pertains to a temporary adjustable bipolar lead.

2. Description of the Prior Art

There has never been a coaxial sliding pacing lead for connecting between a chamber or chambers of a heart and a pulse generator. In the past, it has always been a prior art practice to either securely affix an electrode or electrodes to the walls of the heart or in the alternative, to let the electrode of a pacing lead lie adjacent to the wall.

The present invention overcomes the disadvantages of the prior art problems in providing a temporary adjustable bipolar pacing lead.

SUMMARY OF THE INVENTION

The present invention provides a temporary adjustable bipolar lead for use with external pulse generators for short term pacing of the ventricle, atrium, or both.

According to one embodiment of the present invention, there is provided a temporary adjustable bipolar lead including an inner lead and coaxial outer lead, the inner lead having a quadrafillar space-wound coil with polyurethane insulation, an electrode at one end and a pin connector in plastic bushing mounted at the other end, an outer coaxial lead having a ring electrode at one end, a pin connector at another end and which takes off from the coaxial end of the outer lead, and a self-sealing temporary lead introducer head at the junction of the inner lead and outer lead and including a diameter to accommodate the end of the outer lead at one end of the head, a diaphragm mounted in the other head having a hole with an inner diameter accommodating the inner lead and the end of the outer lead taking off from the side of the head whereby the inner lead is in slideable engagement with the outer lead through the hole of the diaphragm providing spacing of the electrode with respect to the ring electrode.

One significant aspect and feature of the present invention is a pacing lead which provides spacing between the two electrodes for optimum temporary transvenous pacing of right ventricular, atrial or atrial-ventricular pacing.

Another significant aspect and feature of the present invention is a self-sealing temporary lead introducing head which provides for a sterile environment between the lead and the individual user.

A stylet can be utilized with the temporary adjustable bipolar lead of the present invention to facilitate transvenous insertion of the pacing lead.

BRIEF DESCRIPTION OF THE DRAWING

Other objects and many of the attendant advantages of this invention will be readily appreciated as the same becomes better understood by reference to the following detailed description when considered in connection with the accompanying drawing, in which like reference numerals designate like parts throughout the Figure thereof and wherein:

FIG. 1 illustrates a plan view of the temporary adjustable bipolar lead, and;

FIG. 2 illustrates a cross-sectional view taken along line 2—2 of FIG. 1.

DETAILED DESCRIPTION OF THE PREFERRED EMBODIMENT

FIG. 1, which illustrates a plan view of an adjustable bipolar coaxial lead 10, of the present invention, shows an inner lead 12, an outer lead 14, the inner lead 12 coaxially positioned through the outer lead 14 and through a self-sealing temporary lead introducer head 24 as later described in detail. The inner lead 12 includes a coaxial nickel alloy electrical conductor of quadrafillar space-wound coil 16 within an insulating sleeve of polyurethane 22. An electrode 18 of platinum-iridium affixes to one end and a pin connector 20 affixes to the other end. The outer lead 14 includes a coaxial nickel alloy electrical quadrafillar space-wound coil 26 of a larger diameter than that of the coil 16 so as to coaxially position over the coil 16 and includes an insulating sleeve of polyurethane insulation 32. A ring electrode 28 electricially affixes at one end and a pin connector 30 affixes at the other end 14a while a mid portion of the outer lead 14 passes through the self-sealing temporary lead introducing head 24 at the junction 34 as also illustrated in FIG. 2. A stylet 36, including a handle 36a, inserts into and down through the inner lead 12 to the electrode 18 providing for stiffness, curvature and controlled flexibility required to maneuver the lead tip 18 into the right ventricle.

FIG. 2, which illustrates a cross-sectional view taken along lines 2-2 of FIG. 1, shows the self-sealing temporary lead introducing head 24 including a body 24a of polyethelene, a cap 24b for the body 24a also of polyethelene, and a diaphragm 24c of rubber which mounts between the body 24a and the cap 24b and has a hole 24d which slideably accepts the inner lead 12. The body 24a includes circumferential ring projections 24e and a circumferential ring identation 24f for engagement with the diaphragm 24c, and a circumferential ring projection 24m of the cap 24b. Likewise, the cap 24b includes circumferential ring projection 24g which engages against the diaphragm 24c. A longitudinal hole 24h extends outwardly in the body 24a from the other end 14b of the outer lead 14 providing take off of the outer lead 14 at the junction 34. The diameter of the outer lead 14 is reduced as illustrated to a smaller diameter as dictated and abuts up against the circular ring projection 24a in the inner longitudinal hole 24j of the body 24a. The diameter of the longitudinal hole 24j in the body 24a flares out at 24k to an inner diameter 24l.

PREFERRED MODE OF OPERATION

The temporary adjustable bipolar lead 10 is sterilized by an autoclave or other suitable process and can be introduced through a superficial peripheral vein such as with a percutaneous introducer.

The distal end 18 of the lead 10 passes into the vein and through the venous system in the usual manner. Position of the lead may be confirmed by fluoroscopy or intracardiac EKG.

The wire stylet 36 provides a stiffness, curvature and controlled flexibility required to maneuver the lead tip 18 into the right ventricle. A distal curvature may be obtained by inserting a curved stylet into the lumen of the lead. With a stylet in place, the lead is passed by the venous system to the right atrium. The stylet can be partially withdrawn before advancing the distal tip of the lead into the apex of the ventricle thereby avoiding possible perforation of the relatively thin right ventricle wall. Accurate positioning and wedging of the electrode is essential for stable endocardial pacing. A satisfactory position can usually be achieved either with a tip of the lead pointing straight toward the apex or with the distal end of the lead making a slight dip or bend, suggesting that it is curving around a trabeculation. In the atrial position, fluoroscopy may be required to determine that the lead tip is lodged in the atrial appendage or coronary sinus.

Once the lead tip 18 is positioned, the ring electrode 28 may be adjusted until the desired stimulation and/or sensing threshold is obtained. This is accomplished by holding the terminal for the distal tip 18 reinforced by the stylet steady, pushing or pulling the outer lead 14 as is appropriate which will cause a sliding action of the ring electrode with respect to the electrode. Again, fluoroscopy may be required to establish the position of the ring electrode.

Various modifications can be made to the temporary adjustable bipolar lead of the present invention without departing from the apparent scope of the present invention.

Having thus described the invention, there is claimed as new and desired to be secured by Letters Patent:

1. An adjustable bipolar transvenous lead comprising:
    an inner lead having an electrical conductor with an electrode at a first end and an electrical connection at a second end wherein said inner lead is insulated along its outer surface;
    an outer lead having a ring electrode at said first end wherein a first portion of said outer lead is slideably mounted coaxial to said inner lead between said first end and a junction intermediate said first end and said second end and wherein a second portion of said outer lead is not coaxial to said inner lead; and
    a lead introducer slideably mounted to said inner lead at said junction and fixedly mounted to said outer lead at said junction having a body with three apertures wherein said first portion of said outer lead passes through a first aperture, said second portion of said outer lead passes through a second aperture, and said inner lead passes through said third aperture at a point intermediate said junction and said second end and said third aperture is sealed by a rubber diaphragm fixedly mounted to said body through which said inner lead passes.

2. An adjustable bipolar transvenous lead according to claim 1 wherein said outer lead further comprises:
    a space-wound coil having polyurethane insulation along its outer surface.

3. An adjustable bipolar transvenous lead according to claim 1 or claim 2 wherein said inner lead further comprises:
    a space-wound coil with polyurethane insulation permitting use of a coaxial stylet.

* * * * *

UNITED STATES PATENT AND TRADEMARK OFFICE
CERTIFICATE OF CORRECTION

PATENT NO. : 4,271,847
DATED : June 9, 1981
INVENTOR(S) : Kenneth B. Stokes

It is certified that error appears in the above–identified patent and that said Letters Patent are hereby corrected as shown below:

Column 2,
    Line 52, "24a" should be --24i--;

Line 54, "241" should be --24$l$--.

Signed and Sealed this

Twentieth Day of October 1981

[SEAL]

Attest:

GERALD J. MOSSINGHOFF

Attesting Officer     Commissioner of Patents and Trademarks